United States Patent [19]

Ikin

[11] 4,367,047
[45] Jan. 4, 1983

[54] APPARATUS FOR THE DETECTION OF DOWNLINES ON COATED WEB MATERIAL

[75] Inventor: John B. Ikin, Leigh-on-Sea, Great Britain

[73] Assignee: Ciba-Geigy AG, Basel, Switzerland

[21] Appl. No.: 210,956

[22] Filed: Nov. 28, 1980

[30] Foreign Application Priority Data

Dec. 7, 1979 [GB] United Kingdom ............... 7942267

[51] Int. Cl.³ ............................................ G01N 21/84
[52] U.S. Cl. .................................... 356/431; 250/572
[58] Field of Search .................. 356/429, 430, 431; 250/562, 563, 571, 572

[56] References Cited

U.S. PATENT DOCUMENTS

| | | | |
|---|---|---|---|
| 3,206,606 | 9/1965 | Burgo et al. | 250/563 |
| 3,814,945 | 6/1974 | Allnutt et al. | 250/571 |
| 3,845,297 | 10/1974 | Maeda et al. | 250/216 |
| 3,931,525 | 1/1976 | Clarke | 250/572 |
| 4,200,397 | 4/1980 | Sick et al. | 356/429 |
| 4,226,538 | 10/1980 | Van Beeck | 356/430 |

FOREIGN PATENT DOCUMENTS 2150495 4/1973 Fed. Rep. of Germany .

*Primary Examiner*—R. A. Rosenberger
*Attorney, Agent, or Firm*—Harry Falber

[57] ABSTRACT

This invention relates to an apparatus for the detection of downlines on coated web material. The web material is transported past an inspection zone which consists of a means for projecting a narrow beam of light onto the web, means for deflecting the beam of light to scan the web repeatedly in a direction transverse to the direction of web motion, a photocell responsive to light transmitted by the web, an optical diffusing element arranged between the inspection zone and the light sensitive apparatus, and means for moving the diffusing element along a path at least partly transverse to the direction of web transport. Faults are detected by fluctuations in the photocell output.

The diffuser is used so that false signals from scratches on the photocell or slight defects in the web are eliminated and it is moved so as to eliminate defects in the diffuser element surface.

6 Claims, 4 Drawing Figures

APPARATUS FOR THE DETECTION OF DOWNLINES ON COATED WEB MATERIAL

This invention relates to the inspection of coated web material.

In the manufacture of photographic films and papers a very high degree of uniformity is sought during the coating of the silver halide-containing solutions onto the base material. In particular, great care must be exercised to ensure that the quantity of coating solution applied by the coating device varies by less than 2% from point to point across the coated width of the base web. If a local variation occurs exceeding this limit, it will be visible in the photographic material, after exposure and processing, as a streak running down the length of the web. Hereafter such streaks will be referred to as "downlines".

It is known practice to use a flying-spot laser scanner to inspect the quality of coating on web material by cyclically sweeping a narrow beam of light transversely across the web. Photographic coatings on transparent base materials are usually inspected by light transmitted through the material, any variation in coating thickness being detected as a variation in the absorption as scatter of light by the coating.

In microrecording films the emulsion coating is very thin, contains relatively few silver halide crystals per unit area and these crystals are also small. As a result, the coating transmits light freely, absorbing only a small proportion and scattering the transmitted light to only a small degree. Should a downline occur in the coating of such a product, the defect is best detected by arranging the laser-scanner to project a beam onto the web so that the undeviated component transmitted by the web falls directly on a photocell or on a light-gathering means associated with a photocell and extending transverse to the direction of web transport. A variation in coating thickness produces a variation in the degree of scatter of light passing through the film and accordingly a variation in the light flux falling on the photocell. As the laser beam sweeps cyclically transversely across the web, downline defects can then be detected as perturbations in the current from the photocell occurring always at the same point in the transverse sweep.

A practical difficulty arises when dust, scratches or other imperfections produce similar perturbations. These imperfections may be in the photocell itself or on one of the optical components across which the undeviated component of the laser beam sweeps before it reaches the photocell. Because the perturbations from such defects also occur always at the same points in the transverse sweep, they are not readily distinguished from downlines.

A remedy has now been found which comprises diffusing the undeviated component of the transmitted light so that the laser beam does not explore the minute imperfections of the photocell or light-gathering means.

Therefore according to the present invention there is provided an apparatus for the detection of downlines on web material transported past an inspection zone which comprises means for projecting a narrow beam of light onto said web, means for deflecting said beam to scan said web repeatedly in a direction transverse to the direction of web motion, light sensitive means responsive to light transmitted by said web, an optical diffusing element arranged between said inspection zone and said light sensitive means and means for moving said diffusing element along a path at least partly transverse to the direction of web transport.

By diffusing the undeviated component at least in the direction transverse to the web direction, light reaches the photocell by multiple paths simultaneously. A spot of dust or a scratch obstructing one of these paths will make only an imperceptible effect on the photocell output. It will be understood that, whereas the diffuser conceals any small defects in the optical properties of the photocell or its light-gathering means, the presence of dust or scratches on the diffusing element will produce undesirable perturbations in the photocell current. In fact, if the film diffuses transmitted light to only a small degree, the undeviated component of the transmitted laser beam virtually inspects the diffusing element surface for defects. Any defects on the diffusing element surface can however be distinguished by moving the diffusing element, whereupon the apparent position of the defect moves with the diffusing element. A perturbation due to a downline will not move when the diffusing element moves. Thus the present invention is best used with a method of downline detection which responds only to perturbations in the same position on successive transverse sweeps.

The diffusing element may move continuously in one direction along a path transverse to the web, for example it may be in the form of a moving belt or it may be in the form of a disc which rotates in the path of the moving web. However when a wide web is being inspected there are practical problems associated with the use of a diffusing element in the form of a rotating disc or a moving flexible belt. It is accordingly more convenient to arrange the diffusing element in the form of a strip disposed transverse to the direction of web transport which moves in in a cyclic path or which reciprocates in a substantially linear path.

Any dust or debris resting on the diffusing element will lead to optical irregularities which may give rise to fault signals indistinguishable from a downline until the diffusing element is moved. By agitating the diffusing element when fault signals are detected, not only can spurious downlines be differentiated from true downlines but also there is a possibility of detaching the dust or debris from the diffusing element.

According to a further form of the invention, therefore, means are provided for agitating the diffusing element.

In a web inspection system providing automatic detection and logging of the positions of downlines on the web, it may be advantageous to agitate the diffusing element continuously. In this way fault signals can be logged immediately they are detected. This is usually preferable to a system in which, before a downline can be recorded, the origin of the fault signal must first be tested by a trial agitation of the diffusing element.

According to another form of the invention, therefore, means are provided for continuously agitating the diffusing element during inspection of the web.

Movement and agitation of the diffusing element may conveniently be provided by rotation of a shaft by an electric motor. Provided the diffusing element is agitated in the direction transverse to web movement and provided also that the diffusing element is of adequate width, there is no reason why the diffusing element should not also be agitated in the direction of web movement.

According to yet another form of the invention, therefore, means are provided for moving at least one end of the diffusing element in a substantially elliptical path.

An alternative arrangement comprises supporting the diffusing element at either end on leaf springs disposed at right angles to the element. This arrangement has the merit of subjecting no sliding surfaces to wear and generating dust. When suitably energised, the leaf springs vibrate rather in the manner of loaded tuning forks. Energisation may be provided by a solenoid (for shock energisation) or by an electromagnetic vibrator or oscillator of the type used to drive an electrically maintained tuning fork. In some cases, the presence of turbulent air currents may be sufficient to maintain the leaf springs in vibration.

According to an additional form of the invention therefore the diffusing element is supported on leaf springs attached to the two ends at right angles to the length of the element and means are provided for vibrating the leaf springs.

Preferably the optical diffusing element is moved in a direction transverse to the direction of web motion by a distance greater than the effective dimension of the imperfection at the plane of the web, measured in the direction transverse to the direction of web motion.

Practical embodiments of the invention will now be described with reference to FIGS. 1 to 4.

Figure 1:
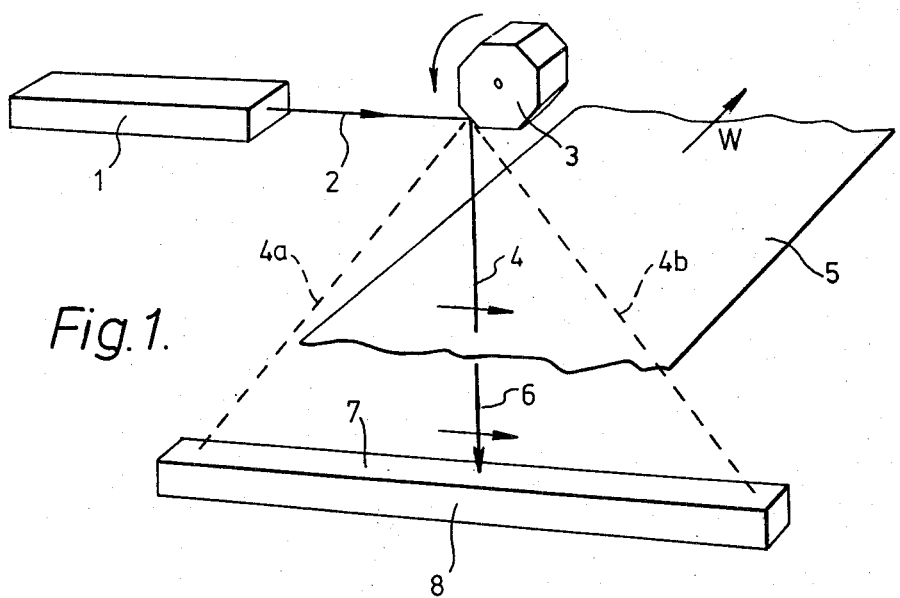
FIG. 1 shows the principal elements of a flying-spot laser scanner according to the known art.

In FIG. 1 a laser 1 projects a light beam 2 onto a rotating mirror polygon 3 from which the reflected beam 4 is swept over a path bounded by 4a and 4b, thereby to explore a path on the web 5 and arranged transversely to the direction of the movement of the web as shown by the arrow W. Part of beam 4 is transmitted by web 5 to fall directly on the entrance window 7 of the box 8 containing a photocell (not shown).

With web materials producing a very low degree of light scatter, beam 6 is sufficiently narrow to be modulated by dust particles and scratches on the window 7. When beam 6 encounters such a dust particle, beam 4 will be always at the same position across the width of the web 5. Thus when the output signal from the photocell is examined there is no way in which the signal due to such a dust particle can be distinguished from the signal due to a downline in the web. Such a distinction might be made by agitating the box 8, but this is usually undesirable because of the size and weight of the box and because it means agitating the electrical leads (not shown) connecting the photocell to items outside the box.

Figure 2:
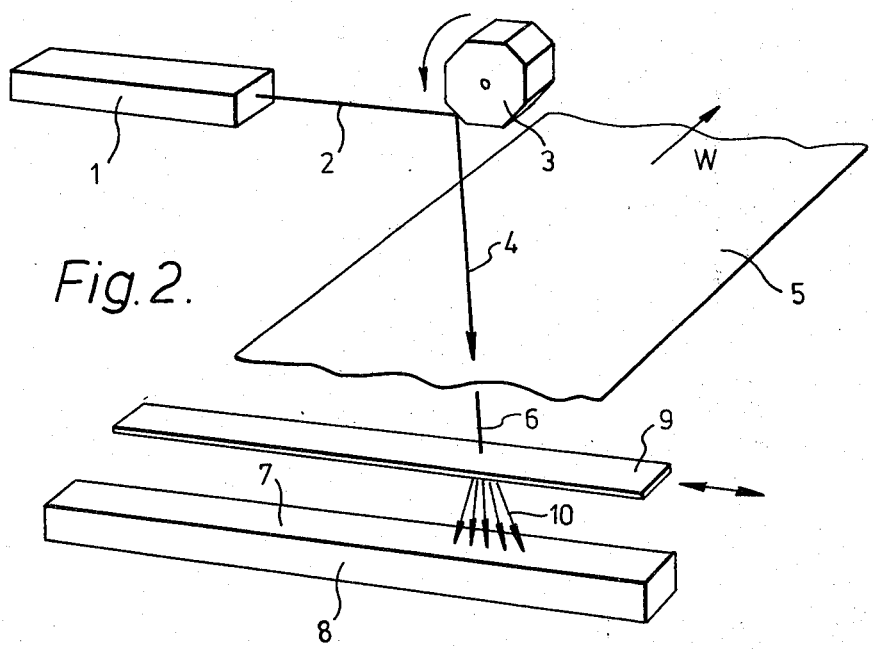
FIG. 2 shows the application of a reciprocating optical diffusing element to a laser scanner of the type shown in FIG. 1.

In FIG. 2 an optical diffusing element 9 has been added to the arrangement shown in FIG. 1. In FIGS. 1 and 2 like numbers indicate like parts. The effect of the diffusing element 9 is to spread the undeviated component 6 of beam 4 so that a bundle of rays 10 falls on the window 7. As beam 4 sweeps across web 5, the bundle 10 sweeps along window 7. Because bundle 10 illuminates a substantial area of window 7 at any time, the effect of a dust particle on window 7 will be negligible. Should a dust particle rest on element 9, in the path of beam 6, however, it will cause a significant disturbance in light passing element 9 and hence in the output current of the photocell in box 8. By reciprocating element 9 as indicated by the double ended arrow in FIG. 2, this disturbance is made to appear at different points in the successive sweeps of beam 4 across web 5. Dust on element 9 is thus readily distinguished from a downline on web 5. This distinction may be made by observing the waveform of photocell current on an oscilloscope synchronised to the sweep of beam 4. On such a display, a true downline will produce a stationary disturbance in the waveform, whereas dust on element 9 will produce disturbances which move in sympathy with element 9.

Figure 3:
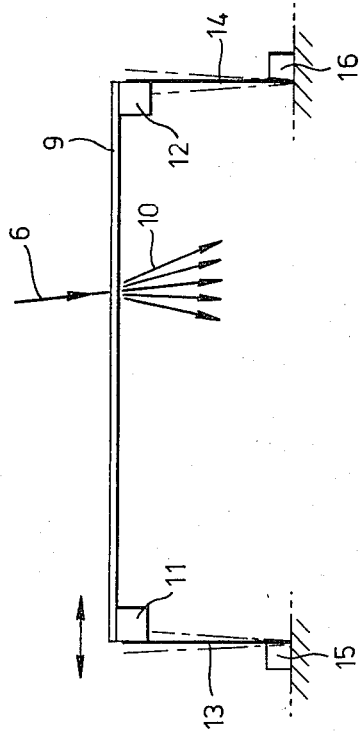
FIG. 3 shows a diffusing element supported on leaf springs.

In FIG. 3, the diffusing element 9 is shown in elevation indicating how beam 6 is diffused into a bundle of rays 10. At either end of element 9 are blocks 11 and 12 to which are attached leaf springs 13 and 14. At their other ends the leaf springs are attached to anchor blocks 15 and 16. Element 9 has thus freedom to move only in a direction parallel to its length, i.e. transverse to the direction of web motion. This method of mounting element 9 is almost free of friction and in some cases the system may be kept in vibration by the turbulent flow of ambient air currents. In other cases the element may be occasionally shock-excited by the impact of a hammer operated, for example, by a solenoid. Alternatively, a electrical contact may be added to block 12 and springs 13 and 14 caused to vibrate in a self-sustaining system similar to that used in a trembler bell or Morse buzzer.

Figure 4:
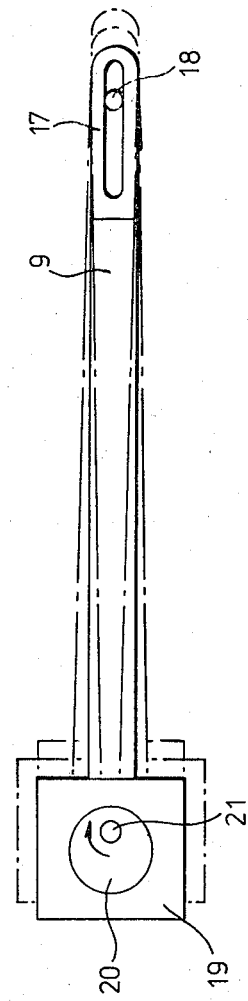
FIG. 4 shows a diffusing element agitated by an eccentric rotating in a trunnion block.

FIG. 4 relates to an alternative embodiment in which a rotary action is used to agitate element 9. In FIG. 4, element 9 is seen in plan view. At one end is attached a slotted member 17 engaging a pin 18. At the other end of element 9 is attached a trunnion block 19 embracing an eccentric 20 attached to shaft 21. A motor (not shown) causes shaft 21 to rotate on its own centre. Rotation of eccentric 20 within trunnion block 19 then causes block 19 to move in a circular path as indicated by the broken lines in FIG. 4. All points on the element 9 will be caused to move left and right in FIG. 4 by a distance equal to the throw of eccentric 20. In addition, each point will move to and fro in the web direction by a distance proportional to the distance from pin 18. This additional movement is of no consequence provided the width of element 9 is made greater than the width of the window (7 in FIG. 2) plus the total throw of the eccentric.

I claim:

1. An apparatus for the detection of downlines on web material transported past an inspection zone which comprises means for projecting a narrow beam of light onto said web, means for deflecting said beam to scan said web repeatedly in a direction transverse to the direction of web motion, light sensitive means responsive to light transmitted by said web, an optical diffusing element arranged between said inspection zone and said light sensitive means and means for moving said diffusing element along a path at least partly transverse to the direction of web transport.

2. An apparatus according to claim 1 wherein the diffusing element is in the form of a strip disposed transverse to the direction of web transport and moves in a cyclic path or reciprocates in a substantially linear path.

3. An apparatus according to claim 2 wherein said means for moving agitate the diffusing element when a fault signal is detected.

4. An apparatus according to claim 2 wherein said means for moving agitate the diffusing element continuously during the inspection of the web material.

5. An apparatus according to any one of claims 2 to 4 wherein means are provided for moving at least one end of the diffusing element in a substantially elliptical path.

6. An apparatus according to any one of claims 2 to 4 wherein the diffusing element is supported on leaf springs attached to the two ends at right angles to the length of the element and means are provided for vibrating the leaf springs.

* * * * *